United States Patent [19]

Mashiba et al.

[11] Patent Number: 4,628,111
[45] Date of Patent: Dec. 9, 1986

[54] N-BENZYLOXYCARBONYL-L-THREONINE AMIDE HEMIHYDRATE

[75] Inventors: Akihiro Mashiba, Tokyo; Kazuteru Hagita, Oomiya; Yoshinobu Miyazawa, Tokyo; Tetsushi Saino, Yono; Yasuhisa Tashiro, Yokohama, all of Japan

[73] Assignee: Nippon Kayaku Kabushiki Kaisha, Tokyo, Japan

[21] Appl. No.: 723,658

[22] Filed: Apr. 16, 1985

[30] Foreign Application Priority Data

Apr. 26, 1984 [JP] Japan ................................. 59-82962

[51] Int. Cl.$^4$ ......................................... C07C 125/065
[52] U.S. Cl. .................................................... 560/159
[58] Field of Search ......................................... 560/159

[56] References Cited

FOREIGN PATENT DOCUMENTS 2071650 9/1981 United Kingdom .

OTHER PUBLICATIONS

Dekker, J. Biol. Chem., 180, pp. 155–173 (1949).

Primary Examiner—Michael L. Shippen
Attorney, Agent, or Firm—Henry C. Nields

[57] ABSTRACT

The present invention relates to new easily filtrable, non-hygroscopic N-benzyloxycarbonyl-L-threonine amide hemihydrate.

1 Claim, 4 Drawing Figures

N-BENZYLOXYCARBONYL-L-THREONINE AMIDE HEMIHYDRATE

BACKGROUND OF THE INVENTION

N-Benzyloxycarbonyl-L-threonine amide (hereinafter referred to as Z-L-Thr-$NH_2$) is useful as a starting material for the synthesis of monocyclic β-lactam antibiotics and is disclosed in the specification of British Patent Laid-Open No. 2,071,650. According to this specification, Z-L-Thr-$NH_2$ was extracted from the reaction mixture with ethyl acetate and then purified and isolated by using a solvent mixture of ethyl acetate and n-hexane.

In experiments conducted according to said process, the inventors have found that the filtration of the intended product was quite difficult and Z-L-Thr-$NH_2$ was obtained in the form of an anhydrous, amorphous powder which was hygroscopic.

The difficulty of the filtration of the substance is a fatal defect in the mass production and the hygroscopicity of the obtained substance is undesirable for the storage and measurement thereof.

SUMMARY OF THE INVENTION

After intensive investigations made for the purpose of overcoming the above-mentioned defects, the inventors have found that easily filtrable, non-hygroscopic Z-L-Thr-$NH_2$ hemihydrate crystals can be obtained by crystallizing Z-L-Thr-$NH_2$ from an aqueous solution thereof.

The present invention has been completed on the basis of this finding.

DETAILED DESCRIPTION OF THE INVENTION

Figure 1:
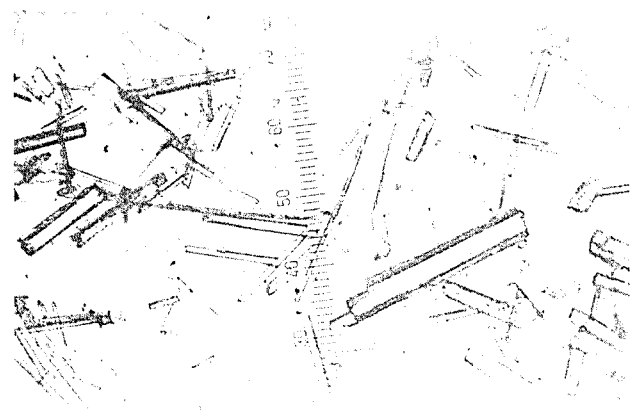
FIG. 1 is a micrograph showing a crystal structure of N-benzyloxycarbonyl-L-threonine amide hemihydrate (hereinafter referred to as Z-L-Thr-$NH_2.\frac{1}{2}H_2O$) obtained in Example 1.
Figure 2:
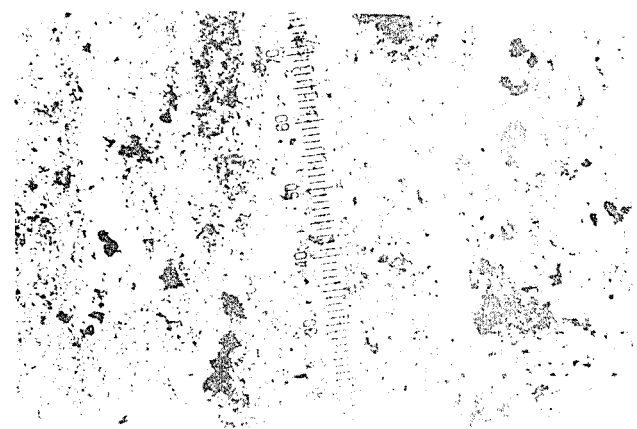
FIG. 2 is a micrograph of Z-L-Thr-$NH_2$ obtained in a referential example.

The physicochemical properties of Z-L-Thr-$NH_2.\frac{1}{2}H_2O$ of the present invention are as follows:

(1) Crystal form:

FIG. 1 shows a microphotograph of Z-L-Thr-$NH_2.\frac{1}{2}H_2O$ obtained in Example 1 of the present invention. It is apparent from this figure that a crystal form of Z-L-Thr-$NH_2.\frac{1}{2}H_2O$ of the present invention is large, clear needles. FIG. 2 shows a microphotograph of Z-L-Thr-$NH_2$ obtained in a referential example (a known process). It is apparent from this figure that this compound is in the form of amorphous powder.

Figure 3:
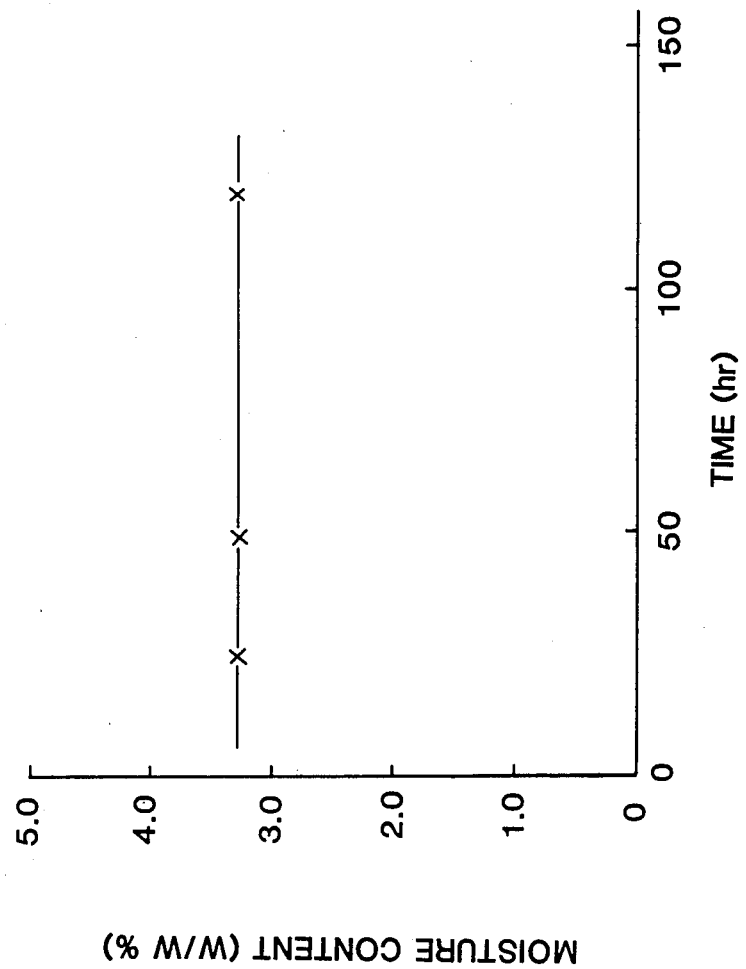
FIG. 3 shows a hygroscopicity curve of Z-L-Thr-$NH_2.\frac{1}{2}H_2O$.

(2) Hygroscopicity:

FIG. 3 shows a hygroscopicity curve of Z-L-Thr-$NH_2.\frac{1}{2}H_2O$ obtained in Example 1 of the present invention as determined at 25° C. and at a relative humidity of 60%. It is understood from this figure that Z-L-Thr-$NH_2.\frac{1}{2}H_2O$ of the present invention is not hygroscopic at all.

Figure 4:
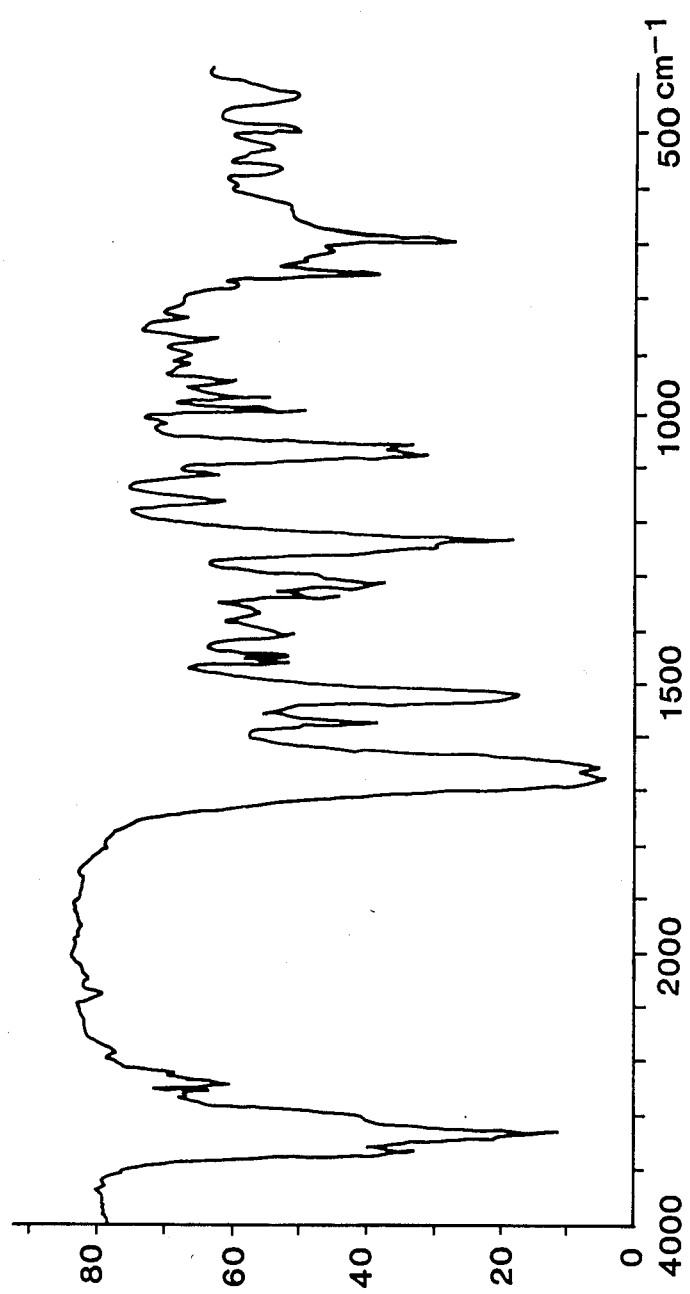
FIG. 4 shows an infrared absorption spectrum of Z-L-Thr-$NH_2.\frac{1}{2}H_2O$.

(3) Infrared absorption spectrum:

FIG. 4 shows an infrared absorption spectrum of Z-L-Thr-$NH_2.\frac{1}{2}H_2O$ of the present invention.

(4) Elementary analysis:

The results of the elementary analysis of Z-L-Thr-$NH_2.\frac{1}{2}H_2O$ of the present invention are shown in Table 1.

TABLE 1

|   | Calculated (%) | Found (%) |
|---|---|---|
| C | 55.16 | 55.23 |
| H | 6.56 | 6.61 |
| N | 10.73 | 10.57 |

(5) Melting point:

Z-L-Thr-$NH_2.\frac{1}{2}H_2O$ of the present invention had a melting point of 82° to 84° C.

A process for producing Z-L-Thr-$NH_2.\frac{1}{2}H_2O$ of the present invention comprises crystallizing Z-L-Thr-$NH_2$ from an aqueous solution thereof.

The aqueous solution used in the present invention is water or a mixture of a hydrophilic organic solvent and water. Examples of the hydrophilic organic solvents include lower alcohols such as methanol, ethanol, n-propanol, isopropanol and n-butanol; ketones such as acetone and methyl ethyl ketone; cyclic ethers such as tetrahydrofuran and dioxan; amides such as dimethylformamide and dimethylacetamide; acetonitrile; and dimethyl sulfoxide.

The mixing ratio of the hydrophilic organic solvent to water in the solvent mixture is up to 2, preferably up to 1 (parts by volume).

The concentration of Z-L-Thr-$NH_2$ in the aqueous solution is about 10 to 70 w/v %, preferably about 20 to 50 w/v %.

Z-L-Thr-NH2 can be crystallized from its aqueous solution by cooling or concentrating the solution. When the solvent for the solution is a mixture of water and a large relative amount of a hydrophilic organic solvent, Z-L-Thr-$NH_2$ can be crystallized by reducing its solubility by adding water to the solution.

The crystallized Z-L-Thr-$NH_2.\frac{1}{2}H_2O$ is filtered and air-dried or dried under reduced pressure at a temperature of up to 50° C.

The solution of Z-L-Thr-$NH_2$ can be obtained by dissolving solid Z-L-Thr-$NH_2$ in the above-mentioned aqueous solvent under heating at a temperature of 30° C. to a boiling point of the solvent, preferably 50° to 80° C.

When the solution of Z-L-Thr-$NH_2$ is impure, the solution is treated with active carbon or the like, if necessary, prior to the above-mentioned process to obtain purified Z-L-Thr-$NH_2.\frac{1}{2}H_2O$.

The filtration of the obtained Z-L-Thr-$NH_2.\frac{1}{2}H_2O$ was completed within, 2 min in the following Example 1, while 25 min was required in the filtration of Z-Thr-$NH_2$ as shown in the following referential example. It is apparent from this fact that Z-L-Thr-$NH_2.\frac{1}{2}H_2O$ of the present invention has a quite excellent filtrability.

Z-L-Thr-$NH_2.\frac{1}{2}H_2O$ of the present invention having thus quite high filtrability can be mass-produced easily. Further, this compound can be handled quite easily, since it is not hygroscopic at all as shown in FIG. 3.

The following examples will further illustrate the process for the production of Z-L-Thr-$NH_2.\frac{1}{2}H_2O$ of the present invention.

EXAMPLE 1

11.8 g (0.1 mol) of L-threonine amide and 16.8 g (0.2 mol) of sodium hydrogencarbonate were added to 350 ml of water to obtain a solution. 17.9 g (0.105 mol) of benzyloxycarbonyl chloride was added slowly to the solution under vigorous stirring at a temperature of up to 20° C. over a period of 30 min. The mixture was stirred at room temperature for additional 5 h and a solid thus formed was filtered, washed and dried to obtain 21.4 g (yield: 85.0 %) of impure solid Z-L-Thr-$NH_2$. 85 ml of water was added to the solid product and heated to 73° C. to obtain a solution. A small amount of an insoluble matter was filtered out and the filtrate was left to cool to room temperature and then cooled to 10° C. in an ice/water bath. Crystals thus formed were filtered and dried at a temperature of up to 40° C. under an aspirator vacuum to obtain 20.0 g of Z-L-Thr-$NH_2 \cdot \frac{1}{2}H_2O$. The filtration time was 2 min.

EXAMPLE 2

50 ml of water was added to 10 g (0.04 mol) of Z-L-Thr-$NH_2$ obtained in a referential example given below. The mixture was heated to 65° C. to obtain a solution. Then, the same treatment as in Example 1 was repeated to obtain 9.0 g of Z-L-Thr-$NH_2 \cdot \frac{1}{2}H_2O$. The filtration time was 1 min.

EXAMPLE 3

A mixture of 1 ml of methanol and 10 ml of water was added to 2.0 g (7.9 mmol) of impure, solid Z-L-Thr-$NH_2$ obtained in the same manner as in Example 1 and heated to 55° C. to obtain a solution. Then, the same treatment as in Example 1 was repeated to obtain 1.85 g of Z-L-Thr-$NH_2 \cdot \frac{1}{2}H_2O$.

EXAMPLE 4

A mixture of 1 ml of tetrahydrofuran and 10 ml of water was added to 2.0 g (7.9 mmol) of impure, solid Z-L-Thr-$NH_2$ obtained in the same manner as in Example 1 and heated to 48° C. to obtain a solution. Then, the same treatment as in Example 1 was repeated to obtain 1.83 g of Z-L-Thr-$NH_2 \cdot \frac{1}{2}H_2O$.

EXAMPLE 5

A mixture of 1 ml of acetone and 10 ml of water was added to 2.0 g (7.9 mmol) of impure, solid Z-L-Thr-$NH_2$ obtained in the same manner as in Example 1 and heated to 52° C. to obtain a solution. Then, the same treatment as in Example 1 was repeated to obtain 1.69 g of Z-L-Thr-$NH_2 \cdot \frac{1}{2}H_2O$.

EXAMPLE 6

A mixture of 1 ml of dimethylformamide and 10 ml of water was added to 2.0 g (7.9 mmol) of impure, solid Z-L-Thr-$NH_2$ obtained in the same manner as in Example 1 and heated to 54° C. to obtain a solution. Then, the same treatment as in Example 1 was repeated to obtain 1.76 g of Z-L-Thr-$NH_2 \cdot \frac{1}{2}H_2O$.

EXAMPLE 7

A mixture of 1 ml of acetonitrile and 10 ml of water was added to 2.0 g (7.9 mmol) of impure, solid Z-L-Thr-$NH_2$ obtained in the same manner as in Example 1 and heated to 52° C. to obtain a solution. Then, the same treatment as in Example 1 was repeated to obtain 1.80 g of Z-L-Thr-$NH_2 \cdot \frac{1}{2}H_2O$.

REFERENTIAL EXAMPLE

An experiment was conducted according to the specification of British Patent Laid-Open No. 2071650 as follows:

11.8g (0.1 mol) of L-threonine amide and 20.0 g (0.24 mol) of sodium hydrogencarbonate were added to 200 ml of water to obtain a solution. A solution of 18.8 g (0.11 mol) of benzyloxycarbonyl chloride in 16 ml of tetrahydrofuran was added slowly over a period of 1 h to said solution under vigorous stirring. The mixture was stirred for additional 16 h and extracted with one 100 ml portion and two 50 ml portions of ethyl acetate.

The extracts were combined together, dried over anhydrous magnesium sulfate and concentrated under reduced pressure. The residue was dissolved in 50 ml of ethyl acetate. 60 ml of n-exane was added to the solution and the mixture was boiled until a transparent solution was obtained. The solution was cooled and amorphous powders thus formed were filtered and dried to obtain 20.8 g (yield: 82.5 %) of Z-L-Thr-$NH_2$. The filtration time was 25 min.

We claim:
1. Non-hygroscopic N-Benzloxycarbonyl-L-threonine amide hemihydrate crystal.

* * * * *